United States Patent
Srinivasan

(10) Patent No.: US 9,931,585 B2
(45) Date of Patent: Apr. 3, 2018

(54) ELECTROLYTIC DEVICE FOR CONTAMINANT REMOVAL AND METHOD

(71) Applicant: DIONEX CORPORATION, Sunnyvale, CA (US)

(72) Inventor: Kannan Srinivasan, Tracy, CA (US)

(73) Assignee: DIONEX CORPORATION, Sunnyvale, CA (US)

(*) Notice: Subject to any disclaimer, the term of this patent is extended or adjusted under 35 U.S.C. 154(b) by 685 days.

(21) Appl. No.: 14/260,095

(22) Filed: Apr. 23, 2014

(65) Prior Publication Data

US 2015/0306518 A1  Oct. 29, 2015

(51) Int. Cl.
| | | |
|---|---|---|
| *B01D 15/36* | (2006.01) | |
| *G01N 30/96* | (2006.01) | |
| *C25F 1/00* | (2006.01) | |
| *C25F 7/00* | (2006.01) | |
| *B01D 61/44* | (2006.01) | |
| *G01N 30/28* | (2006.01) | |

(52) U.S. Cl.
CPC ......... *B01D 15/367* (2013.01); *B01D 15/361* (2013.01); *B01D 61/44* (2013.01); *C25F 1/00* (2013.01); *C25F 7/00* (2013.01); *G01N 30/96* (2013.01); *G01N 30/28* (2013.01); *G01N 2030/965* (2013.01)

(58) Field of Classification Search
CPC .... G01N 30/96; G01N 2030/965; C07K 1/18; B01D 15/361–15/363; B01D 15/367
See application file for complete search history.

(56) References Cited

U.S. PATENT DOCUMENTS

| | | | |
|---|---|---|---|
| 4,999,098 A | | 3/1991 | Pohl |
| 5,045,204 A | * | 9/1991 | Dasgupta ........... B01D 19/0031 204/257 |
| 8,367,423 B2 | | 2/2013 | Liu et al. |
| 2003/0127392 A1 | | 7/2003 | Srinivasan et al. |
| 2003/0132163 A1 | | 7/2003 | Srinivasan et al. |

(Continued)

FOREIGN PATENT DOCUMENTS

| | | |
|---|---|---|
| CN | 1809407 A | 7/2006 |
| WO | 02071052 A2 | 2/2003 |

OTHER PUBLICATIONS

U.S. Appl. No. 14/028064 to Srinivasan et al., entitled "Electrolytic Four-Channel Device and Method," filed Sep. 16, 2013.

*Primary Examiner* — Ibrahime A Abraham
*Assistant Examiner* — Salil Jain

(57) ABSTRACT

An electrolytic device comprising a housing includes at least first and second adjacent liquid flow-through channels. A barrier impermeable to ion flow and to bulk liquid flow is disposed between the first and second channels. A first electrode assembly is disposed adjacent to one end of the channels and a second electrode assembly is disposed adjacent the other end of the channels.

Also, a contaminant removal method using the above electrolytic device. A first aqueous stream including contaminants flows through the first channel while passing a current between the first and second electrode assemblies to remove contaminants. Effluent from the first channel flows, with or without further treatment, through the second channel while passing current between said first and second electrode assemblies to remove further contaminants.

16 Claims, 10 Drawing Sheets

(56) References Cited

U.S. PATENT DOCUMENTS

2004/0048389 A1 3/2004 Liu et al.
2006/0231404 A1 10/2006 Riviello
2014/0069176 A1 3/2014 Liu et al.

* cited by examiner

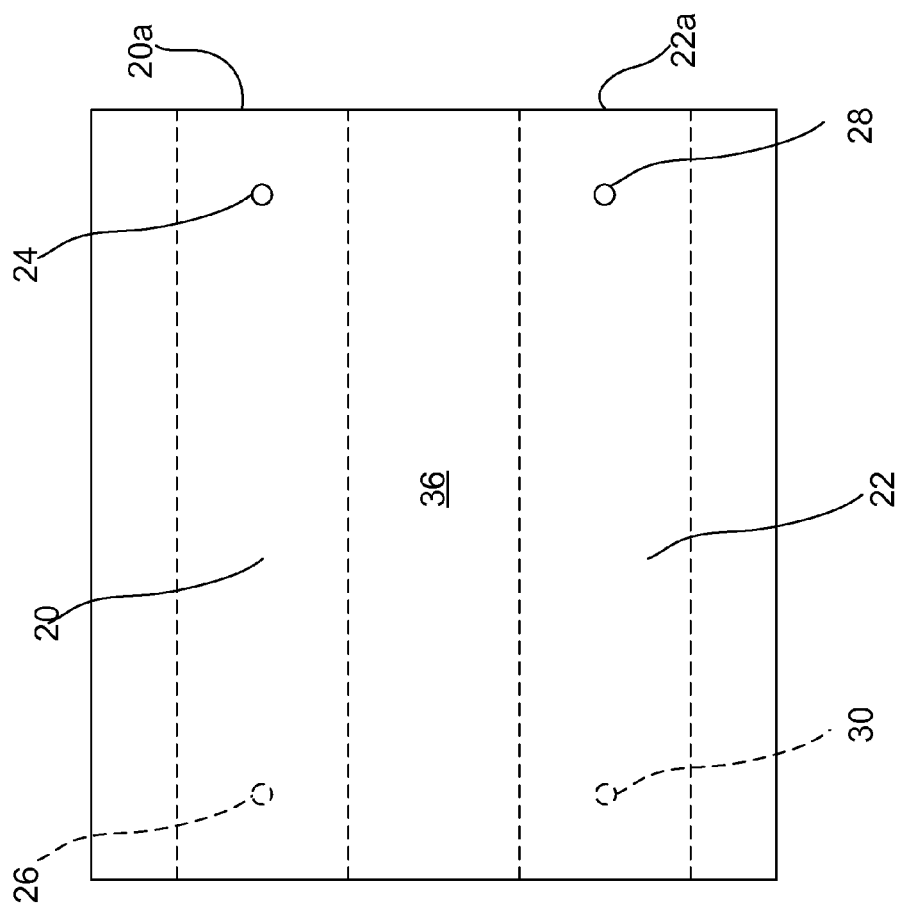
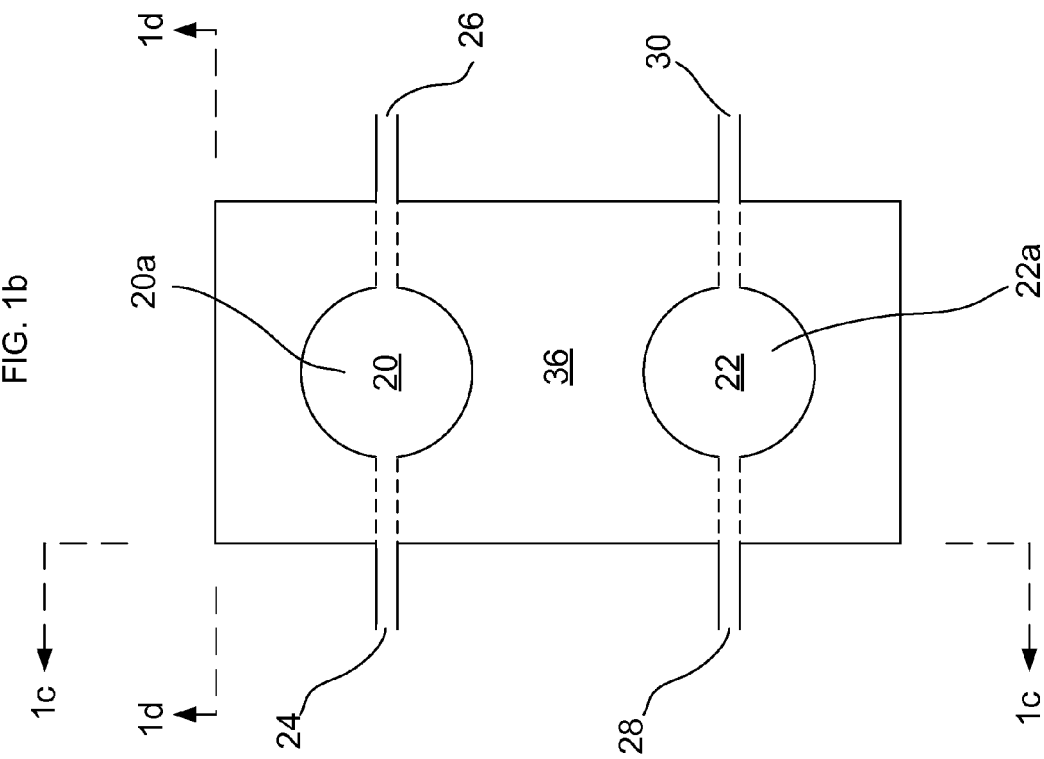

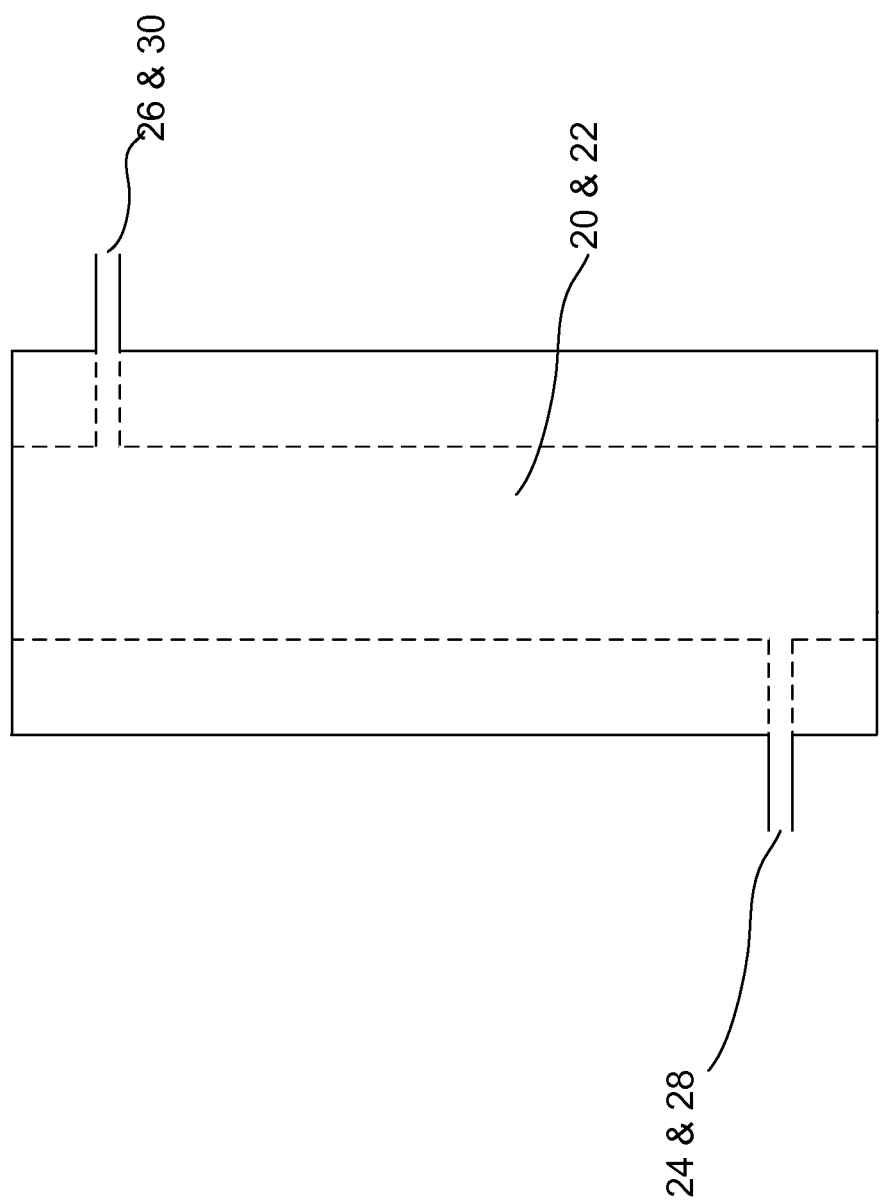

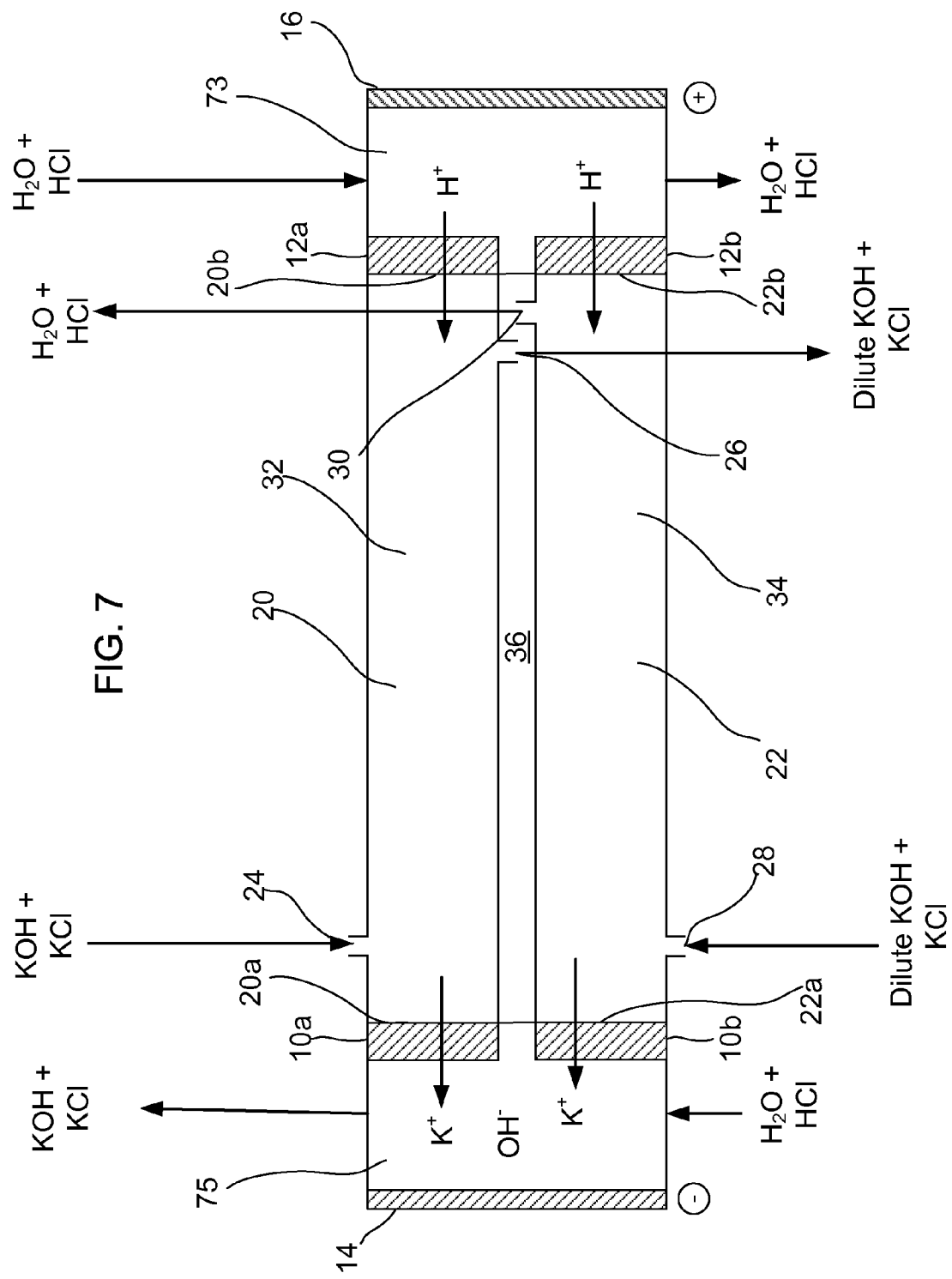

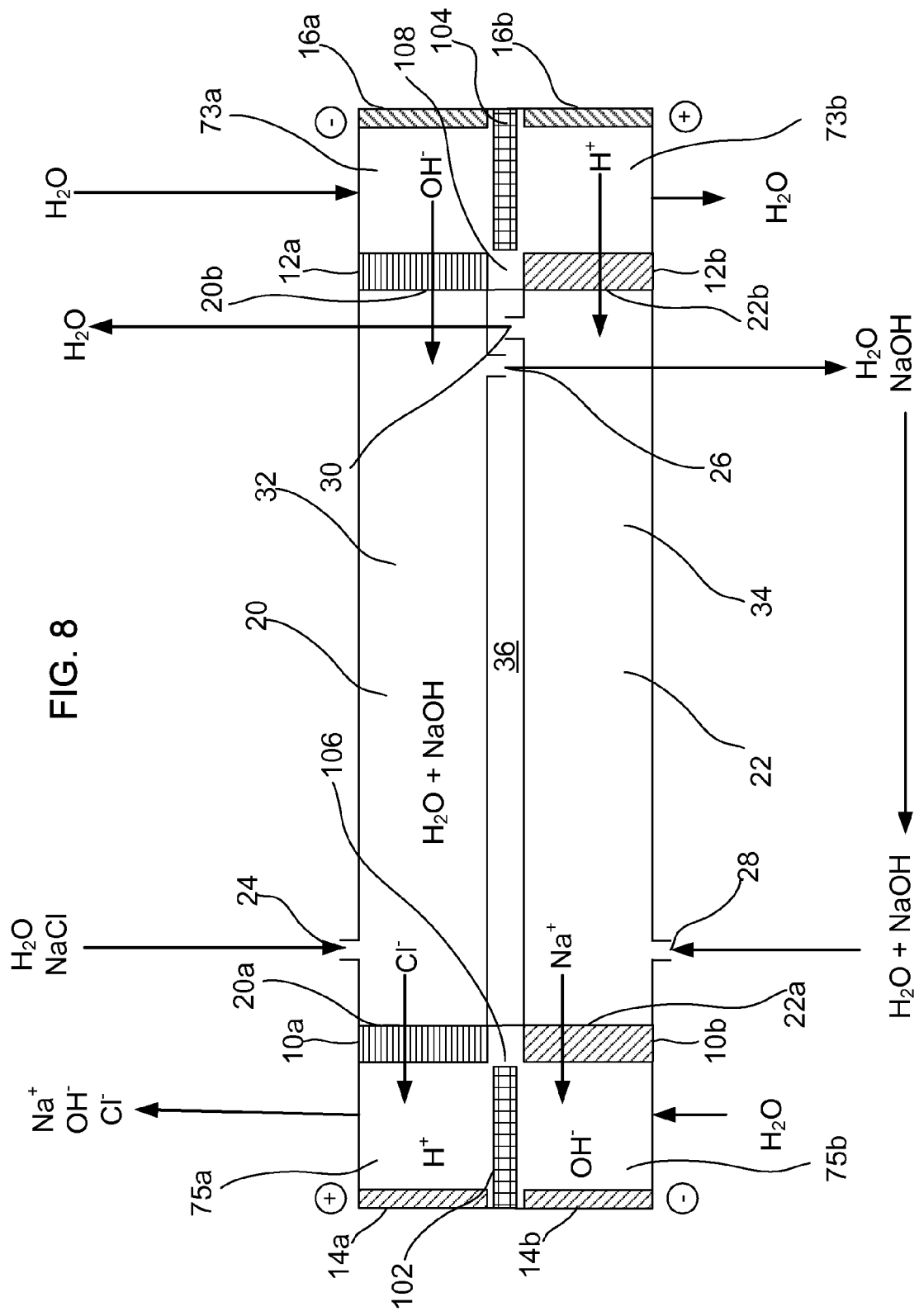

ELECTROLYTIC DEVICE FOR CONTAMINANT REMOVAL AND METHOD

BACKGROUND OF THE INVENTION

The present invention relates to an electrolytic device for contaminant removal suitable for use in a liquid chromatographic system.

Suppressed ion chromatography is a known technique for analysis of sample ions of one charge in an eluent containing electrolyte. First, the sample ions in the eluent are chromatographically separated. Then, the eluent is suppressed by removal of the electrolyte counterions to the sample ions, and the sample ions are detected, typically by an electrical conductivity detector. One type of suppressor device, called a sandwich membrane suppressor, is described in U.S. Pat. No. 4,999,098 (the "'098 patent"). In one embodiment, the suppressor includes three channels. During suppression, the eluent and separated sample ions flow through the central channel of the suppressor while regenerant solution flows in the two outside channels. The outside two channels are separated from the central channel by barriers having exchangeable ions capable of passing ions of only one charge, positive or negative, and of blocking bulk liquid flow. Suitable barriers are ion-exchange membranes sold under the trademark Nafion®. One embodiment is an electrolytic, three-channel flat membrane suppressor illustrated in FIGS. 2 and 3 of the '098 patent. For an anion analysis, the eluent including the analyte anions which have been previously separated on a chromatographic column, comprising a packed bed of anion exchange resin, flows through the central channel. The ion-exchange membranes include exchangeable cations. Eluent cations are removed from the central channel and are drawn toward the negative electrode across the adjacent membrane barrier, as illustrated in FIG. 3 of the '098 patent. Thus, if sodium hydroxide is used as the electrolyte of the eluent, the sodium ion is removed from the central channel across the cation exchange membrane adjacent to the cathode. A device of this type has also been used for purposes other than suppression such as pretreatment of a liquid sample prior to chromatographic separation.

An electrolytic device suitable for use in a liquid chromatography system is disclosed in co-pending U.S. application Ser. No. 14/028,064, filed Sep. 16, 2013. The device comprises a housing including at least first, second, third, and fourth side-by-side liquid flow-through channels, each having an inlet and an outlet. The channels are separated from each other by charged membrane barriers having exchangeable ions capable of passing ions of only one charge, positive or negative, and of blocking bulk liquid flow. A first electrode is disposed adjacent to and along the first channel in electrical communication therewith; and a second electrode is disposed adjacent to and along the fourth channel in electrical communication therewith. The device is disclosed for use in a number of applications such as sample stream pretreatment, and eluent suppression.

The presence of ionic contaminants leads to performance problems when pursuing ion chromatography. It can affect the background which can impact the absolute response. For example, for anion analysis when the contaminant is carbon dioxide the background after suppression is carbonic acid, a weak acid which results in low response for all anions. Varying backgrounds can impact the reproducibility of the separation since the analyte response would vary resulting in errors in quantitation. The quantitation of the peak of interest could be compromised by a changing background making it difficult to draw baselines in order to integrate the peaks of interest. Also, contaminant peaks vary in concentration from run to run and day to day. This makes quantitation of analytes of interest very difficult particularly under trace analysis conditions. Overall, inconsistent baselines and blanks can result in poor reproducibility of the analysis and lead to errors in quantitation.

In chromatography systems sold by Dionex Corporation under the tradename RFIC, a continuously regenerated trap column is used for contaminant removal. The device is electrolytically regenerated and uses a DC potential to achieve the contaminant removal. A DC power supply is therefore needed for device operation. The contaminants are removed via an ion exchange membrane. The device can be installed on the high pressure side of an eluent generator or can be installed before an eluent generator but after the pump. In the former placement, the device removes contaminants from the eluent stream which comprises contaminants from deionized water, eluent generation or the pumping process. In the latter placement, the device removes contaminants only from the influent deionized water stream. Other devices such as a deionizer or water purifier can be used to remove the contaminants stemming from the influent deionized stream before the pumping process. These devices are effective only when operated with a flowing stream because storing purified water and retaining it contaminant free is challenging. These devices, however, do not address contaminants stemming from other sources such as storage containers, pump seals, pumps etc.

It has been discovered that when operating a device in the eluent stream, highly retained components on the contaminant removal device, such as a polymeric anions are accumulated. When this occurs, the removal of small ionic contaminant such as carbonate becomes difficult since the capacity of the phase is not fully available for the contaminant removal process. Under these conditions the competing effects of the eluent favors elution of the smaller contaminants which adversely affects chromatographic performance. Using two devices for the contaminant removal function such as two continuously regenerated trap columns, one before the eluent generator and one after, is not desirable as this doubles the costs with the use of two devices and two power supplies.

SUMMARY

In one embodiment, an electrolytic device is provided comprising a housing including at least first and second adjacent liquid flow-through channels, each channel having first ends and second ends, an inlet adjacent the upstream end of each channel and an outlet adjacent the downstream end of each channel. The first ends are adjacent to each other and second ends are adjacent to each other. A first barrier impermeable to ion flow and to bulk liquid flow is disposed between the first and second channels. A first electrode assembly is disposed adjacent to both first ends and in electrical communication with said first and second channels; and a second electrode assembly is disposed adjacent to both of said second ends in electrical communication with said first and second channels.

In another embodiment, a contaminant removal method is provided using the foregoing electrolytic device. The method comprises flowing a first aqueous stream including contaminants to the inlet of the first channel and therethrough to the outlet thereof while passing a current between the first and second electrode assemblies to remove contaminants from the first aqueous liquid stream. Effluent from the first channel, with or without further treatment, flows to the second channel inlet therethrough to the outlet thereof while passing current between the first and second electrode assemblies to remove further contaminants from the first effluent.

BRIEF DESCRIPTION OF THE DRAWINGS

FIG. 1b is a simplified end view of the electrolytic device of FIG. 1a without the ion exchange barriers and electrodes. Ports 24 and 28 are more forward facing with respect to ports 26 and 30.

FIG. 1c is a simplified side view of the electrolytic device without the ion exchange barriers and electrodes from the perspective of arrows 1c of FIG. 1b. Ports 24 and 28 are located on an opposing face with respect to ports 26 and 30.

FIG. 1d is a simplified top view of the electrolytic device of FIG. 1a without the ion exchange barriers and electrodes from the perspective of arrows 1d of FIG. 1b. Ports 26 and 30; ports 24 and 28; and channels 20 and 22 are in an eclipsing configuration.

FIG. 2 is a schematic view of a chromatography system with an eluent generator using the device of FIG. 1a.

FIGS. 3-8 are schematic views of electrolytic devices according to the present invention.

DETAILED DESCRIPTION OF EMBODIMENTS

In general, the present invention relates to an electrolytic device for contaminant removal including at least two channels separated by a barrier impermeable to ion flow and bulk liquid flow and use of the device, e.g., in a liquid chromatography system.

Figure 1A:
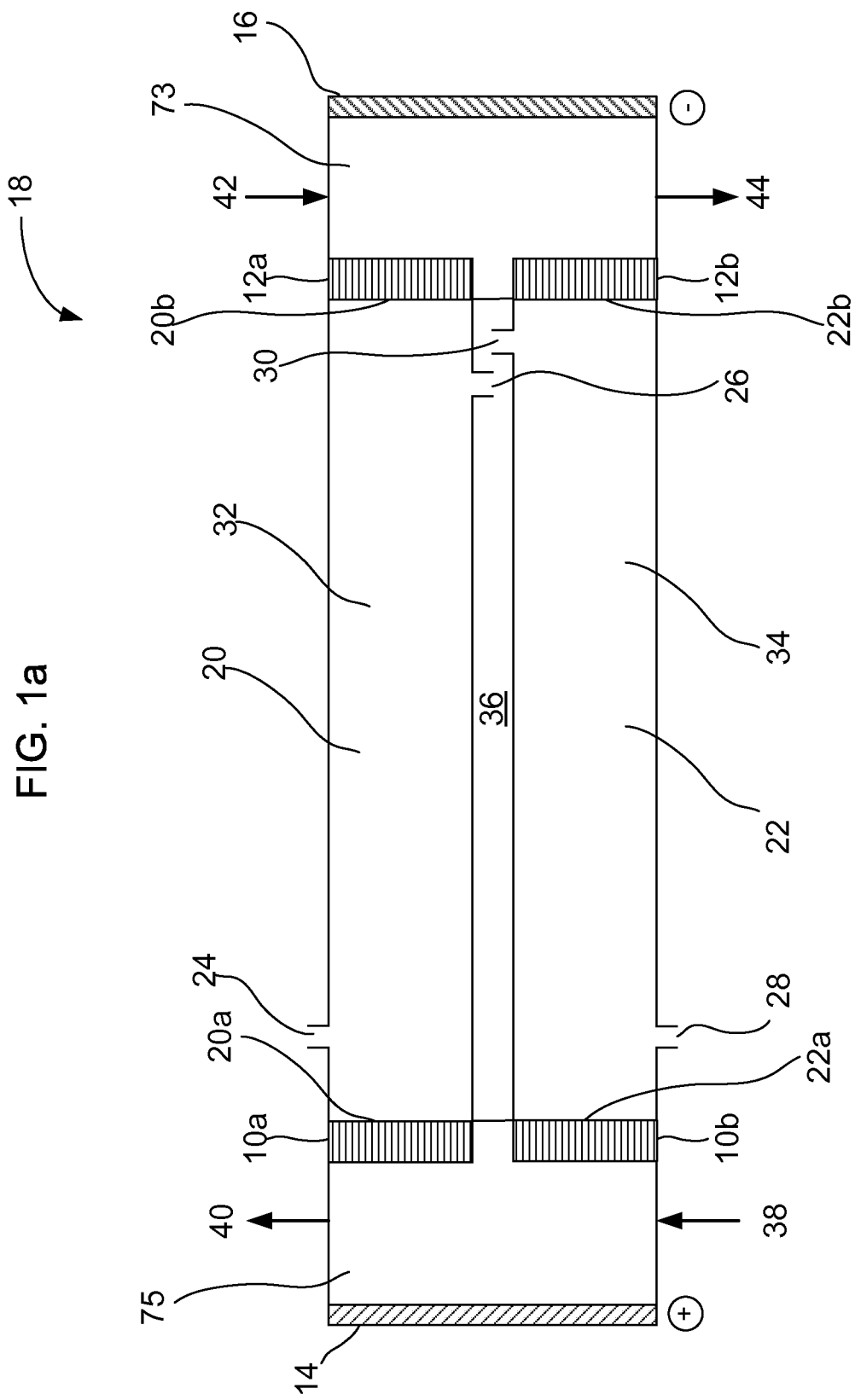
FIG. 1a is a simplified schematic view of an electrolytic device according to the invention.

FIG. 1a illustrates a schematic view of an electrolytic device 18 according to the invention. Device 18 includes a housing, not shown, such as of the type illustrated in FIG. 2 of the '098 patent with suitable ports for the fluidic inlets and outlets. Device 18 defines first and second side-by-side liquid flow channels 20 and 22, each having an inlet and an outlet. A first channel 20 has first and second ends 20a and 20b, respectively, includes inlet port 24 and outlet port 26. Second channel 22 has first and second ends 22a and 22b, respectively, and includes inlet port 28 and outlet port 30. Inlet ports 24 and 28 are adjacent to the upstream ends of channels 20 and 22, respectively, and outlet ports 26 and 30 are adjacent the downstream ends of channels 20 and 22, respectively. Channels 20 and 22 are adjacent, side-by-side liquid flow-through channels. The first ends 20a and 22a are adjacent to each other and the second ends 20b and 22b are adjacent to each other. Channel 20 is separated from channel 22 by a barrier 36, extending along the liquid flow path through the channels. Bather 36 is impermeable to ion flow and to bulk liquid flow and blocks electric communication. In one embodiment, the housing is made by machining channels in a block of PEEK and the barrier is residual material in the block. In an alternative design channels 20 and 22 can be defined by solid tube materials such as PEEK A first electrode assembly 14 is disposed adjacent to both first ends 20a and 22a. A second electrode assembly 16 is disposed adjacent to both second ends 20b and 22b. When describing the electrode assemblies, the term "adjacent" excludes disposing the assemblies along the path of flow through channels 20 and 22. Electrode assemblies 14 and 16 may be in direct contact with the liquid flowing through channels 20 and 22, respectively, or may be separated from such liquids, so long as the electrodes are in electrical communication with the liquid flowing through channels 20 and 22, respectively. For example, in FIG. 1a, electrode assemblies 14 and 16 are separated from channels 20 and 22 by ion exchange barrier assembly portions 10a, 10b, and 12a, 12b, described below. In operation electrode assemblies 14 and 16 are connected to a conventional power source, not shown, so that, when the power is turned on, an electric field is applied between the electrode assemblies through the liquid flowing in both channels. At the anode, water is electrolyzed to hydronium ion and oxygen gas and at the cathode water is electrolyzed to hydroxide ion and hydrogen gas.

Figure 6:
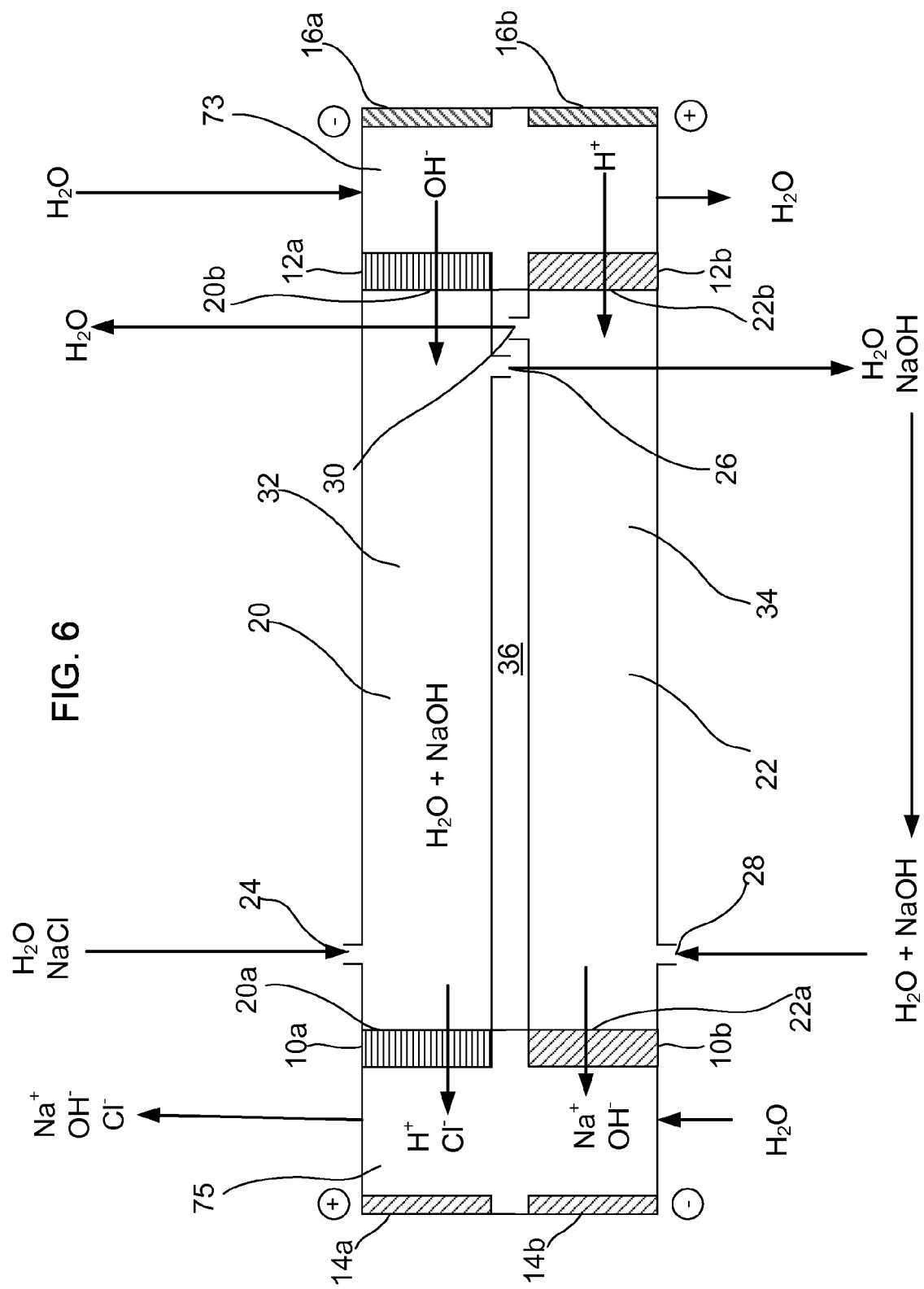

The term "electrodes assembly" encompasses a single continuous electrode, such as electrode 14 adjacent to both first ends 20a and 22a, and a single continuous electrode 16 adjacent to both second ends 20b and 22b as illustrated in FIG. 1a. Alternatively, the term electrode assembly encompasses a first electrode portion adjacent to first end 20a and a spaced second electrode portion adjacent first end 22a and a similar spaced electrode portions, not shown, adjacent second ends 20b and 22b. Such split electrodes are illustrated in FIG. 6, described below. In the split electrode portion alternative, the electrode portions adjacent the first ends can be connected to the same polar side of a power source and the electrode portions adjacent the second ends can be connected to the opposite polar side of the power source. In other embodiments the split electrodes can be connected to an opposite polar side of a power source at the first and second ends. Preferably, the electrode assemblies are made of a noble metal such as platinum.

Similarly, the term "ion exchange barrier assembly" encompasses, as illustrated, one ion exchange barrier portion 10a adjacent to first end 20a and another ion exchange barrier portion 10b adjacent to first end 22a, and one ion exchange barrier portion 12a adjacent to second end 20b and another ion exchange barrier portion 12b adjacent to second end 22b. Further, the term encompasses a single first continuous ion exchange barrier, not shown, adjacent both first ends 20a and 22a and a second continuous ion exchange barrier adjacent second ends 20b and 22b. The ion exchange barriers can have anion exchange or cation exchange functionalities.

The ion exchange barriers are disposed between the electrode assemblies and the first and/or second ends of channels 20 and 22 and permit ion transport but block bulk liquid flow at the first ends and second ends so that bulk liquid is blocked from flow into the regeneration channels. The ion exchange barriers may be of the same type as the ion exchange membranes illustrated in the '098 patent. The sides of the ion exchange barriers opposite the first and second ends can define one wall of a flow-through channel for regenerant aqueous solution.

The functions of the ion exchange barriers are to prevent bulk flow but allow transport of ions, contaminant and/or electrolytically generated regenerant ions. The configuration shown in the present invention permits continuous regeneration of the multiple liquid flow through channels.

In one embodiment of FIG. 1a, channels 20 and 22 are filled with medium comprising packed beds 32 and 34 of anion exchange flow-through resin particles. The electrode assemblies (electrodes 14 and 16) are connected to an external DC power supply (not shown) so that electrode 14 is an anode and electrode 16 is a cathode. As illustrated, device 18 is suitable for contaminant removal of anions. Polarities of the electrode assemblies, ion exchange barriers and medium can be reversed for cation contaminant removal. In other embodiments, the ion exchange barriers are of opposite charge to each other and/or the medium includes exchangeable cations and anions.

Figure 2:
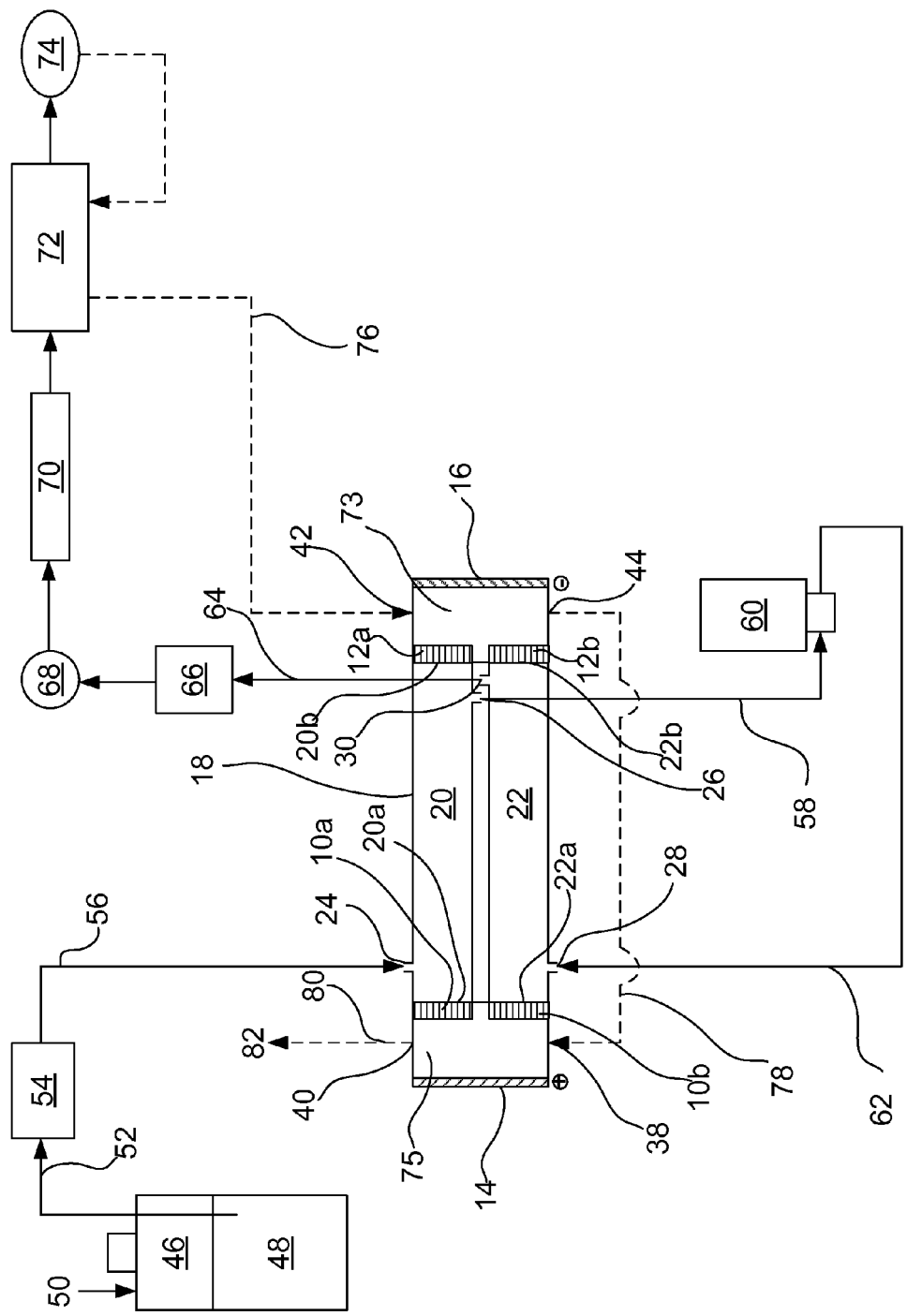

FIG. 2 illustrates a schematic system using generator contaminant removal device 18 in an ion chromatography system, which includes an electrolytic eluent generator, for anion analysis. Reservoir 46 stores an aqueous solution, e.g. deionized water 48, and is connected via line 52 to a pump 54. An optional source of inert gas 50, preferably nitrogen gas, can be provided to pressurize the contents of the reservoir 46. The effluent (output) from pump 54 is connected via line 56 to inlet port 24 of channel 20 in device 18. The outlet port 26 is connected via line 58 to the inlet port of an electrolytic eluent generator 60, e.g., of the type illustrated in U.S. Pat. Nos. 6,225,129 and 8,367,423. The outlet port of generator 60 is connected via line 62 to the inlet port 28 of channel 22. The outlet port 30 of channel 22 is connected via line 64 to an optional degasser module 66, e.g. of the EGC Degas module type from Thermo Fisher Scientific, Sunnyvale, Calif., which removed any residual gases from the aqueous stream. The outlet of the degasser is connected to a standard sample injection port 68 for a conventional chromatography separator (chromatography column) 70. The plumbing is similar to a conventional ion chromatography (IC) system such as illustrated in the '098 patent; thus, the outlet from injection port 68 is connected to separator 70, then to a suppressor 72 and then to a conductivity cell 74, in fluid communication therewith.

The outlet of conductivity cell 74 is plumbed in a recycle mode to a regenerant flow channel of suppressor 72. The waste effluent from the suppressor 72, e.g. of the type shown in the '098 patent, is routed via line 76 through regenerant port 42 of device 18 for a first regenerant channel 73 separated from channels 20 and 22 by ion exchange barrier portions 12a and 12b and then flows out outlet port 44. Inlet port 42 is located in close proximity to the inlet of the first regenerant channel 73 of device 18. Outlet port 44 of first regenerant channel 73 is connected to the inlet regenerant port 38 of a second regenerant channel 75. The liquid flows through second regenerant channel 75 and out outlet port 40. A line 80 is connected to the outlet port 40 and is used to divert the regenerant liquid stream to waste 82. The waste stream from 82 could be used for other purposes such as providing an aqueous stream for the degasser 66.

The two ends of channels 20 and 22 may be sealed using suitable end fittings (not shown) with inlet and outlet ports 38, 40 on one side and 42 and 44 on the other side of the channels. These ports can be used for transporting the aqueous stream required for the electrolytic reactions and to transport out any reaction products at the electrode surfaces.

In the above description a recycle effluent is used to provide water required for the operation of the electrolytic device 18 of the present invention. It should be noted that an independent source of external water stream can be used to regenerate the suppressor 72 and the effluent can be routed to device 18 as described above. Alternate embodiments could use an independent stream of deionized water and routed to channels 73 and 75.

Flow-through structure such as neutral screens, or charged screens of the same charge as the exchangeable ions of the barriers not shown, may be disposed in one or more of channels 20 and 22 such as of the type described in the '098 patent. Also, a bed of neutral particles or ion exchange particles may be disposed in the channels. Preferably, the flow-through structure is flow-through ion exchange medium 32 and 34 such as a packed bed with frits at the outlets which can be loaded, as is conventional, using a vacuum or pressure. Alternate embodiments could also include neutral monolithic structures or functionalized monolith structures in the channels with characteristics similar to the screens or particles described above. In addition, flow-through structures such as neutral screens or particles, or charged screens or ion exchange particles, may be disposed in one or more of regenerant channels 73 and 75.

The device of FIG. 1a can be used for contaminant removal in various liquid analysis systems which share the following common steps. An aqueous stream including contaminants flows to the inlet 24 of channel 20 and through channel 20 while passing a current between the first and second electrode assemblies to remove contaminants from the channel. Effluent from channel 20 flows, with or without further treatment, to channel 22 and through it to outlet 30 while passing a current between the electrode assemblies to remove further contaminants in channel 22. The first and second electrode assemblies can be connected to a single power source and both channels can be in a single device.

In one embodiment, illustrated in FIG. 2, the first channel effluent is further treated prior to flowing to the second channel by flowing through an electrolytic eluent generator, e.g. of the type illustrated in U.S. Pat. No. 8,367,423, in which eluent is generated. The generated eluent flows to inlet 22a of channel 22.

In another embodiment, flow-through ion exchange medium having both exchangeable cations and anions is disposed in the first and second channels. The device may also include the first and second ion exchange barriers described above which may include exchangeable ions of the same or different charge or both. In this device, both cation and anion contaminants can be removed.

Figure 3:
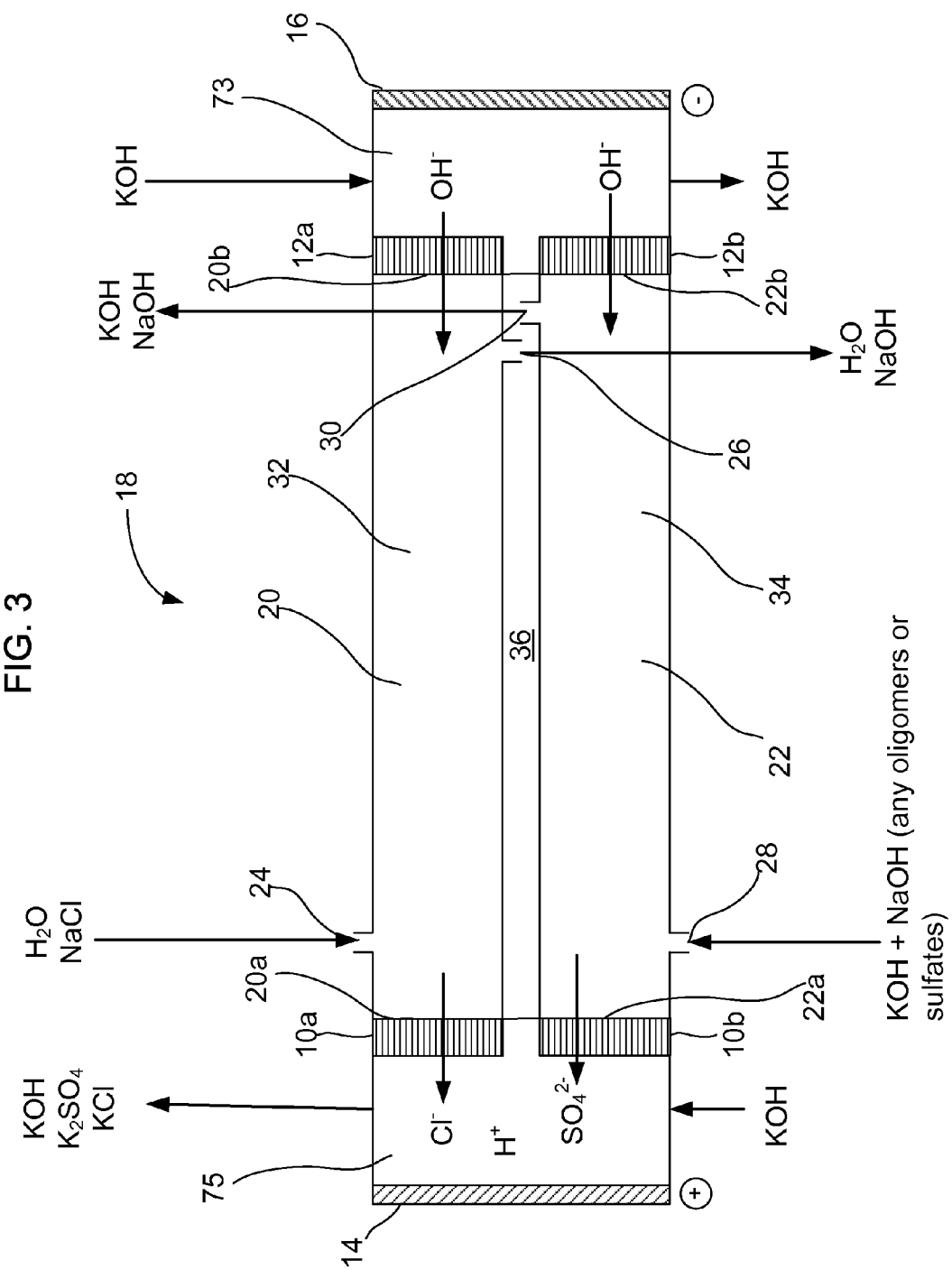

FIG. 3 shows a schematic of device 18 illustrating contaminant removal in the system of FIG. 2 which includes an electrolytic eluent generator. The illustrated aqueous solution is deionized water with a low level of sodium chloride contamination. In operation, when greater than about 1.5 volts is applied, electrolysis results in formation of hydronium ions at the anode and hydroxide ions at the cathode. The chloride ion is retained on anion exchange resin at the inlet of the channel 20 and exchanges for hydroxide ion. Thus, sodium chloride is transformed to sodium hydroxide. Any residual carbonate present as bicarbonate will also be removed in this setup by exchanging bicarbonate anion for hydroxide. The ion exchange medium surface is regenerated by the transport of the electrolytically generated hydroxide along the channel 20. These hydroxide ions combine with electrolytically generated hydronium ions at the anode to form water. The anions in this design will traverse anion exchange membrane barrier portions 10a and 10b and combine at the electrode assembly to form the respective acids. The anode supplies the hydronium required for this reaction.

Next, the purified aqueous stream is routed to an electrolytic eluent generator and forms a KOH eluent in response to an applied current across the electrolytic eluent generator (EGC) cartridge. The eluent containing a small amount of sodium and other species such as sulfate and sulfonated oligomers enters channel 22 in the contaminant removal device 18. The anionic oligomers are all removed in channel 22 and a pure base is produced. As discussed above for channel 20, the surface of the ion exchange medium in channel 22 is regenerated by the transport of the electrolytically generated hydroxide in channel 22. These hydroxide ions combine with electrolytically generated hydronium ions at the positively charged (anode) electrode assembly 14 to form water. The anions in this design will traverse the anion exchange membrane barrier portions port 10a and 10b into regenerant channel 75 and combine at the electrode to form the respective acids. The anode electrode assembly 14 supplies the hydronium required for this reaction. The water required for the electrolysis reactions is preferably derived from the suppressor waste stream and this is routed through the regenerant channels of the contaminant removal device. Alternate embodiments include an external stream of deionized water for the regenerant channels of the contaminant removal device of the present invention.

The illustrated embodiment uses generated base (KOH) as the eluent for anion analysis. However, acid eluents can be used for cation analysis as described in the '098 patent. In this embodiment all functionalities of the ion exchange materials and electrode polarities are reversed to facilitate removal of cationic contaminants.

In the above description of FIG. 3, the two ion exchange bed medium 32 and 34 are analogous to two resistors in parallel. When voltage is applied, the total current is distributed between the two resistors.

Figure 4:
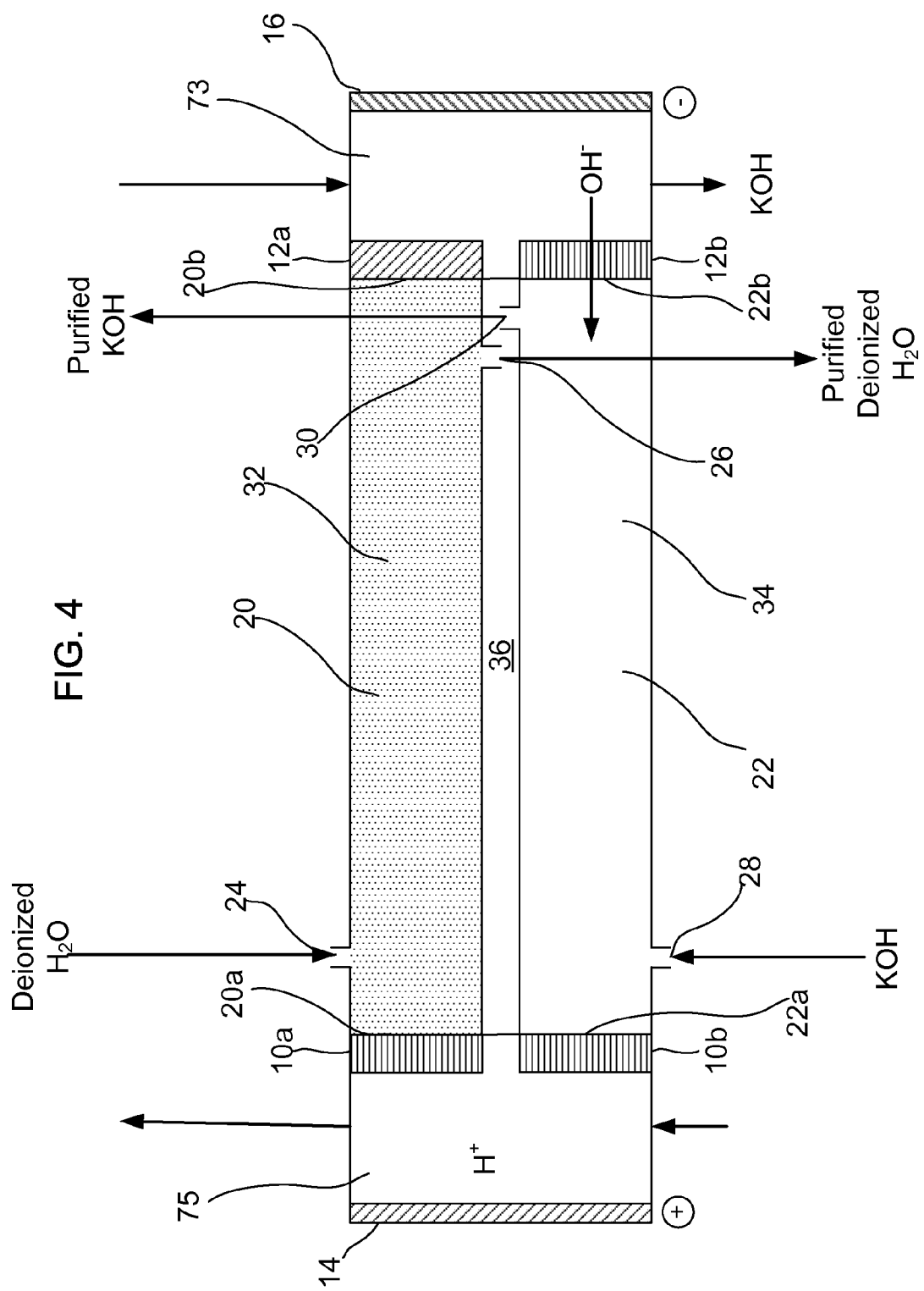

FIG. 4 is another contaminant removal embodiment of the present invention. All parts of device 18 are similar to that of FIG. 1a and are designated with like numbers. The ion exchange barrier portions 10a, 10b and 12b are all anion exchange membranes. Portion 12a is a cation exchange membrane. Channels 20 and 22 are packed with medium 32 and 34 comprising beds of mixed cation exchange and anion exchange particles; and anion exchange particles, respectively. Electrode assemblies 14 and 16 are connected to an external DC power supply (not shown) so that electrode assembly 14 is an anode and electrode assembly 16 is a cathode. In this embodiment channel 20 would remove both anionic and cationic contaminants, such as sodium and chloride, which are converted to water. Medium 32 is regenerated by having anionic contaminants in channel 20 traverse anion exchange barrier portion 10a to anode 14, which is driven by the applied electric field. Cationic contaminants in channel 20 traverse cation exchange barrier portion 12a to cathode 16, which is driven by the applied electric field. Channel 22 removes any residual anionic impurities in the eluent as previously discussed.

Device 18 is suitable for contaminant removal and can be plumbed into an ion chromatography system as shown and discussed regarding FIG. 2.

Figure 5:
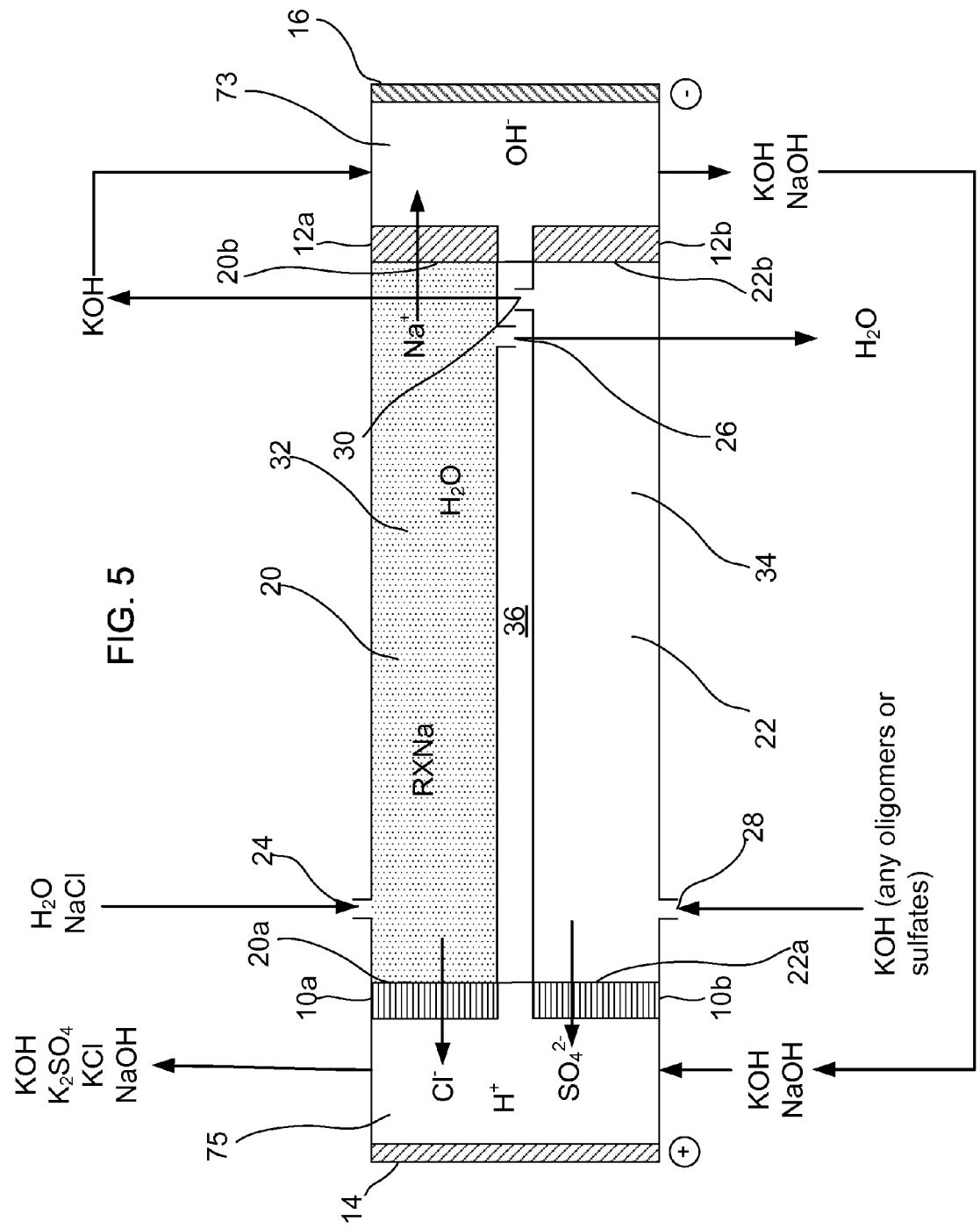

FIG. 5 shows a schematic of contaminant removal device 18 of the present invention. The aqueous solution is deionized water with a low level of sodium chloride contamination. In operation, when greater than 1.5 volts is applied, electrolysis results in formation of hydronium ions at the anode and hydroxide ions at the cathode. The chloride ion is retained on anion exchange resin particles of the mixed (anion and cation exchange) bed medium 32 at the inlet of channel 20 and exchanges for hydroxide ion. Similarly, the sodium ion is retained on the cation exchange resin particles of the mixed bed medium at the inlet of the channel 20 and exchanges for hydronium ion. Thus, sodium chloride is transformed to water. Any residual carbonate present as bicarbonate will also be removed in this setup by transforming the species to water by exchanging bicarbonate anion for hydroxide. The surface of the anion exchange resin medium 32 can be regenerated by the transport of hydroxide ions from the water splitting reaction along channel 20. It should be noted that the voltage applied across medium 32 coupled with the intrinsic dissociation of water into hydronium and hydroxide causes water to be split on the inside of channel 20. These hydroxide ions combine with electrolytically generated hydronium ions at the anodic form electrode assembly 14 to form water. Similarly, the surface of the cation exchange resin medium would be regenerated by the transport of hydronium ions from the water splitting reaction. These hydronium ions combine with electrolytically generated hydroxide ions at the cathode form electrode assembly 16 to form water. The anions in this design will traverse the anion exchange membrane portions 10a and 10b, and combine at the electrode assembly 14 to form acids. The anode supplies the hydronium required for this reaction. The cations will traverse the cation exchange membrane portion 12a and 12b, and combine at the electrode assembly 16 to form the respective base. The cathode supplies the hydroxide required for this reaction. Next the purified aqueous stream is routed to an eluent generator and forms a KOH eluent in response to an applied current across the electrolytic eluent generator. Eluent purification occurs similar to the description for FIG. 3.

Referring back to FIG. 5, $H_2O$ and NaCl flow into inlet port 24 and exit outlet port 26 where the contaminant NaCl is removed. $H_2O$ from outlet port 26 can then be inputted into an eluent generator. The output of the eluent generator flows into inlet port 28 and exits outlet port 30 where contaminants such as oligomers and/or sulfates are removed. The purified eluent from outlet port 30 is in fluid communication with a chromatography column and a detector. After the separation and detection, the effluent can be directed to regenerant chamber 73 to sweep out cationic contaminants. Next, the effluent can be directed to regenerant chamber 75 to sweep out anionic contaminants.

FIG. 6 is yet another example of a contaminant removal device according to the invention. All parts of the contaminant removal device 18 are similar to FIG. 1a and designated with like numbers. Ion exchange barrier portions 10a and 12a are anion exchange membranes and portions 10b and 12b are cation exchange membranes. Channels 20 and 22 are packed with ion exchange resin medium, anion exchange resin for medium 32 for channel 20 and cation exchange resin for medium 34 in channel 22. The electrode assemblies are split in this embodiment so they include electrode portion 14a and 14b and 16a and 16b. The electrode portion however could be powered using one power supply by combining, for example, electrodes 14a with 16b and connecting this to the anode of the power supply and portions 14b and 16a for the cathode electrode. The regenerant ports are interconnected thus requiring only one inlet and outlet on each side of the conduit. In this arrangement, at an applied voltage, the electrodes in channel 73 generate the electrolysis ions and the net reaction is the formation of electrolysis gases hydrogen and oxygen in the aqueous stream. As illustrated in FIG. 6, the contaminants (sodium and chloride) are removed in the vicinity of the electrodes in channel 75. Cationic contaminants are removed as a base while anionic contaminants are removed as acids. In this embodiment the output from port 26 is directly routed to channel 22 for purification. When a constant voltage is applied across the electrodes, the current is divided or distributed across the channels 20 and 22.

In an alternative embodiment, the fluidic pathway between electrode portions 14a and 14b; and also electrode portions 16a and 16b can be fluidically constrained to reduce the likelihood that the electrolytically generated hydroxide and hydronium within each of chambers 73 and 75 do not recombine. FIG. 8 illustrates an electrolytic device that includes a first fluidically constrained barrier 102 to form electrode chambers 75a and 75b; and a second fluidically constrained barrier 104 to form electrode chambers 73a and 73b. A first fluidically constrained pathway 106 is formed between electrode chambers 75a, 75b and proximate to an end portion of first fluidically constrained barrier 102. A second fluidically constrained pathway 108 is formed between electrode chambers 73a, 73b and proximate to an end portion of second fluidically constrained barrier 104. This allows the electrolytically generated hydroxide and hydronium in regenerant chambers 73a and 73b to traverse ion exchange barrier portions 12a and 12b, respectively. Although FIG. 8 illustrates fluidically constrained pathways 106 and 108 proximate to an end portion of a fluidic barrier, a fluidically constrained pathway may also be provided with a first and second barrier each spanning across chambers 73 and 75, respectively, where each barrier contains a relatively small orifice (not shown). Alternatively, a fluidically constrained pathway may also be provided with a first and second barrier spanning across chambers 73 and 75, respectively, where chambers 75a and 75b are fluidically joined by a first conduit and chambers 73a and 73b are fluidically joined by a second conduit (not shown).

For an incoming stream of deionized water containing sodium chloride as a contaminant in channel 20, the device would exchange the chloride for hydroxide ions thus forming an aqueous stream containing sodium hydroxide. The electrolytically generated hydroxide ions regenerate the anion exchange resin in channel 20. When the effluent of channel 20 is routed to channel 22 removal of cations occur due to exchange with hydronium ions on the cation exchange resin thus resulting in formation of contaminant free deionized water. The ion exchange membranes and ion exchange media are continuously regenerated by transport of electrolysis ions. For example, close to anion exchange membrane 12a, cathode 16a generates hydroxide ions which are routed through the membrane 12a via anion exchange particles 32 in channel 20 through anion exchange membrane 10a before reaching the anode 14a. This transport of hydroxide ions along with anions regenerates the ion exchange functionality of membrane 12a and ion exchange particles 32. Similarly, the electrode portion 16b, close to the cation exchange membrane 12b, generates hydronium ions which are routed through the membrane 12b via the cation exchange particles 34 in channel 22 though the cation exchange membrane 10b before reaching the cathode 14b. In this design, channel 20 removes all anions while channel 22 removes all cations. The contaminant removal device 18 of FIG. 6 is thus a water purifier.

FIG. 7 is an example of a suppressor embodiment for anion applications. The ion exchange membrane portions 10a, 10b, 12a and 12b are cation exchange membranes. Channels 20 and 22 are packed with beds of cation exchange resin particles. Electrode assemblies 14 and 16 permit full regeneration of this device.

In operation of the device of FIG. 7, when the voltage exceeded 1.5 volts due to the electrolysis reaction, formation of hydronium and hydroxide ions occurred at the electrode surfaces. The hydronium ions are used for regenerating the ion exchange medium in channels 20 and 22 and are transported from the anode towards the cathode. At the cathode, formation of water occurs from the reaction of the transported hydronium ions with hydroxide ions. In this example, the eluent is partially suppressed in channel 20 and fully suppressed in channel 22. The analyte chloride in this case is converted to hydrochloric acid, a more conductive form. The device can be operated in the recycle mode of operation.

As is clear from the description above, the device of the present invention has many applications including contaminant removal, water purification, and suppression.

The above description refers to a device with two channels 20 and 22 as illustrated in FIGS. 1a to 1d. However, the invention encompasses a device with three or more side-by-side channels separated by barriers impermeable to ion flow and bulk liquid flow.

In order to illustrate the present invention, the following non-limiting examples of its practice are given.

Example 1

A device of the type illustrated in FIG. 1a was used as a contaminant removal device in an ion chromatograph for anion analysis. The device was plumbed as shown in FIG. 2 with channel 20 upstream of the KOH eluent generator and channel 22 downstream from the KOH eluent generator. This plumbing configuration resulted in contaminant free eluent generation. The column was a 4×250 mm IonPac AS15 column from Thermo Fisher Scientific. The suppressor was a 4 mm AERS suppressor also from Thermo Fisher Scientific. The suppressor was operated in the recycle mode as shown in FIG. 2. The contaminant removal device was powered with a DC power supply at 24 V. The system was tested with a gradient comprising of 1 to 50 mM KOH for a run duration of 15 minutes. The gradient program is listed below

| Step | Time | Concentration |
|------|------|---------------|
| 1 | −5.0 minutes | 1 mM KOH |
| 2 | 0 minutes | 1 mM KOH |
| 3 | 15 minutes | 50 mM KOH |
| 4 | 20 minutes | 50 mM KOH |

The baseline drift which is an indication of contaminant removal showed less than 30 nS/cm drift over a 15 minute time period for a gradient concentration of 1 mM to 50 mM KOH. This baseline drift is approximately 4 fold lower than a typical baseline drift with a standard trap column of the prior art. It is believed that the removal of contaminants from the liquid source before the input into the eluent generator and from the output of the eluent generator, provided a significantly more pure eluent and, in turn, a lower baseline drift, than the situation where only the output of the eluent generator was purified.

Example 2

A device of FIG. 1a was used as a contaminant removal device in an ion chromatograph for cation analysis. The device was assembled with membranes 10a, 10b, 12a and 12b in cation exchange form. The packing material (a bed of ion exchange particles) 32 and 34 was a 8% crosslinked cation exchange resin. The electrode 14 was a cathode and electrode 16 was an anode. The device was plumbed as shown in FIG. 2 with channel 20 upstream of the MSA eluent generator 60 and channel 22 downstream from the MSA eluent generator 60. This plumbing configuration resulted in contaminant free eluent generation. The column was a 4×250 mm IonPac CS12A column from Thermo Fisher Scientific. The suppressor was a 4 mm CERS suppressor also from Thermo Fisher Scientific. The suppressor was operated in the recycle mode as shown in FIG. 3. The contaminant removal device was powered with a DC power supply at 24 V. The system was tested with a gradient comprising of 1 to 50 mM MSA for a duration of 15 minutes. The gradient program is listed below.

| Step | Time | Concentration |
|------|------|---------------|
| 1 | −5.0 minutes | 1 mM MSA |
| 2 | 0 minutes | 1 mM MSA |
| 3 | 15 minutes | 50 mM MSA |
| 4 | 20 minutes | 50 mM MSA |

The baseline drift which is an indication of contaminant removal showed less than 20 nS/cm drift over a 15 minute time period for a gradient concentration of 1 mM to 50 mM MSA. This baseline drift is approximately 4 fold lower than a typical baseline drift with a standard trap column of the prior art. Similar to the comments above, Applicant believes that the removal of contaminants from the liquid source before the input into the eluent generator and from the output of the eluent generator, provided a significantly more pure eluent and, in turn, a lower baseline drift, than the situation where only the output of the eluent generator was purified.

What is claimed is:

1. An electrolytic device comprising
a housing including at least first and second adjacent liquid flow-through channels, each channel having an upstream end and a downstream end,
an inlet adjacent said upstream end of each channel and an outlet adjacent said downstream end of each channel,
said upstream ends being adjacent to each other and said downstream ends being adjacent to each other;
a barrier impermeable to ion flow and to bulk liquid flow disposed between said first and second channels;
a first electrode assembly disposed adjacent to both of said upstream ends; and
a second electrode assembly disposed adjacent to both of said downstream ends, in which said first electrode assembly and said second electrode assembly are configured to apply an electric field a) between said first electrode assembly and second electrode assembly, and b) through said first and second channels.

2. The electrolytic device of claim 1 in which said first channel outlet is in fluid communication with said second channel inlet.

3. The electrolytic device of claim 1 further comprising a first ion exchange barrier assembly, which permits ion transport and blocks bulk liquid flow disposed adjacent both of said upstream ends, between said first electrode assembly and both of said upstream ends.

4. The electrolytic device of claim 3 in which said first ion exchange barrier assembly comprises a first barrier portion adjacent to said upstream end of said first channel and a second barrier portion adjacent to said upstream end of said second channel.

5. The electrolytic device of claim 3 further comprising a second ion exchange barrier assembly, which permits ion transport and blocks bulk liquid flow disposed adjacent said downstream ends, between said second electrode assembly and both of said downstream ends.

6. The electrolytic device of claim 5 in which said first and second ion exchange barrier assemblies comprise exchangeable ions of a same charge.

7. The electrolytic device of claim 6 in which said first and second ion exchange barrier assemblies comprise exchangeable ions of opposite charge.

8. The electrolytic device of claim 1 further comprising flow-through ion exchange medium in said first and second channels.

9. The electrolytic device of claim 1 in which said first and second electrode assemblies are connected to a single power supply.

10. The electrolytic device of claim 1 in which said first and second electrode assemblies comprise a first single continuous electrode and a second single continuous electrode, respectively, said first single continuous electrode is adjacent to both of said upstream ends of said first and second channels, and said second single continuous electrode is adjacent to both of said downstream ends of said first and second channels.

11. The electrolytic device of claim 1 in which said first electrode assembly comprises a first electrode portion adjacent to said upstream end of said first channel and a second electrode portion spaced from said first electrode portion and adjacent to said upstream end of said second channel.

12. The electrolytic device of claim 11 in which said second electrode assembly comprises a third electrode portion adjacent said downstream end of said first channel and a fourth electrode portion spaced from said third electrode portion and adjacent to said downstream end of said second channel.

13. A contaminant removal method using an electrolytic device comprising
a housing including at least first and second adjacent liquid flow-through channels, each channel having an upstream end and a downstream end,
an inlet adjacent said upstream end of each channel and an outlet adjacent said downstream end of each channel,
said upstream ends being adjacent to each other and said downstream ends being adjacent to each other;
a barrier impermeable to ion flow and to bulk liquid flow disposed between said first and second channels;
a first electrode assembly disposed adjacent to both said upstream ends; and
a second electrode assembly adjacent to both of said downstream ends of said first and second channels, in which said first electrode assembly and said second electrode assembly are configured to apply an electric field a) between said first electrode assembly and second electrode assembly, and b) through said first and second channels; said method comprising
flowing a first aqueous stream including contaminants to said inlet of said first channel and therethrough to said outlet thereof while passing a current between said first and second electrode assemblies to remove contaminants from said first aqueous liquid stream;
flowing said first aqueous liquid stream from said first channel, with or without further treatment, to said second channel inlet therethrough to said outlet thereof while passing current between said first and second electrode assemblies to remove further contaminants from said first aqueous liquid stream.

14. The method of claim 13 in which said first aqueous liquid stream is further treated prior to flowing to said second channel inlet, said further treatment comprising flowing said first aqueous liquid stream through an electrolytic eluent generator and generating eluent therein and flowing said generated eluent to said second channel inlet.

15. The method of claim 13 in which said electrolytic device further comprising flow-through ion exchange medium in said first and second flow-through channels, said ion exchange material in said first channel including exchangeable cations and anions, said electrolytic device further comprising a first ion exchange barrier assembly which permits ion transport and blocks bulk liquid flow disposed adjacent said upstream ends between said first electrode assembly and said upstream ends, and a second ion exchange barrier assembly which permits ion transport and blocks bulk liquid flow disposed adjacent both of said downstream ends between said second electrode assembly and said downstream ends; wherein said method further comprises removing anion and cation contaminants from said flowing aqueous stream in said first channel.

16. The method of claim 15 in which said first and second ion exchange barrier assemblies include exchangeable ions of a same charge.

\* \* \* \* \*